(12) United States Patent
McFarland, II et al.

(10) Patent No.: US 11,346,025 B2
(45) Date of Patent: May 31, 2022

(54) ARTICLE WITH AT LEAST ONE LAYERED POD

(71) Applicant: NIKE, Inc., Beaverton, OR (US)

(72) Inventors: William C. McFarland, II, Portland, OR (US); Leah M. Resneck, Durham, NC (US); Nikita A. Troufanov, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 138 days.

(21) Appl. No.: 16/054,132

(22) Filed: Aug. 3, 2018

(65) Prior Publication Data

US 2019/0037967 A1 Feb. 7, 2019

Related U.S. Application Data

(60) Provisional application No. 62/541,500, filed on Aug. 4, 2017.

(51) Int. Cl.
*D04B 1/12* (2006.01)
*D04B 1/10* (2006.01)
(Continued)

(52) U.S. Cl.
CPC .......... *D04B 1/123* (2013.01); *A43B 23/025* (2013.01); *D04B 1/10* (2013.01); *D04B 1/16* (2013.01);
(Continued)

(58) Field of Classification Search
CPC ...... A43B 23/026; A43B 23/0225; A43B 1/04
See application file for complete search history.

(56) References Cited

U.S. PATENT DOCUMENTS

| 709,734 | A | * | 9/1902 | Bellis | ....................... D04B 1/24 66/196 |
| 2,108,925 | A | * | 2/1938 | Raynor | .................. D04B 1/123 66/190 |

(Continued)

FOREIGN PATENT DOCUMENTS

| CN | 101772599 B | 4/2013 |
| CN | 104106882 A | 10/2014 |

(Continued)

OTHER PUBLICATIONS

International Search Report and Written Opinion dated Nov. 19, 2018, for corresponding PCT Application No. PCT/US2018/045163 (13 pp.).

(Continued)

*Primary Examiner* — Megan E Lynch
(74) *Attorney, Agent, or Firm* — Shook, Hardy & Bacon L.L.P.

(57) ABSTRACT

In one aspect, the present disclosure provides knitted component comprising with a first surface and a second surface, the first surface facing opposite the second surface. A pod may have the first surface and the second surface, and an edge region may have the first surface and the second surface, where the edge region at least partially demarcates the pod. A first yarn may substantially form the first surface of the pod, where the first yarn is a fusible yarn. A second yarn may substantially form the second surface of the pod, and the second yarn may substantially form the first surface of the edge region.

19 Claims, 8 Drawing Sheets

(51) Int. Cl.
  *A43B 23/02*  (2006.01)
  *D04B 1/16*  (2006.01)
  *A43B 1/00*  (2006.01)
  *A61P 35/00*  (2006.01)
  *A61K 9/00*  (2006.01)
  *A61K 9/16*  (2006.01)
  *A61K 31/05*  (2006.01)
  *A43B 1/04*  (2022.01)

(52) U.S. Cl.
  CPC .............. *A43B 1/0072* (2013.01); *A43B 1/04* (2013.01); *A61K 9/0019* (2013.01); *A61K 9/1611* (2013.01); *A61K 31/05* (2013.01); *A61P 35/00* (2018.01)

(56) References Cited

U.S. PATENT DOCUMENTS

| | | | |
|---|---|---|---|
| 2,372,497 A | | 3/1945 | Johnson et al. |
| 3,964,277 A | * | 6/1976 | Miles ............... D04B 9/16 66/190 |
| 5,299,435 A | * | 4/1994 | Whalley ............ D04B 1/123 66/190 |
| 6,854,296 B1 | * | 2/2005 | Miller, III ........ D04B 1/123 66/190 |
| 7,774,956 B2 | | 8/2010 | Dua et al. |
| 8,448,474 B1 | * | 5/2013 | Tatler ................ D04B 1/123 66/64 |
| 8,745,895 B2 | | 6/2014 | Sokolowski et al. |
| 8,881,430 B2 | * | 11/2014 | Seamarks .......... A43B 23/0245 36/45 |
| 8,997,529 B1 | * | 4/2015 | Podhajny ............ A43B 1/04 66/177 |
| 8,997,530 B1 | * | 4/2015 | Podhajny ............ A43B 1/04 66/177 |
| 9,226,548 B2 | * | 1/2016 | Follet ................. B32B 5/06 |
| 2002/0152776 A1 | | 10/2002 | Didier |
| 2006/0048413 A1 | * | 3/2006 | Sokolowski ....... A43B 23/0235 36/45 |
| 2010/0175276 A1 | * | 7/2010 | Dojan ................. A43B 3/26 36/47 |
| 2012/0233882 A1 | * | 9/2012 | Huffa ................. A43B 1/04 36/45 |
| 2012/0234052 A1 | * | 9/2012 | Huffa ................. D04B 1/123 66/64 |
| 2012/0279260 A1 | * | 11/2012 | Dua .................... D04B 1/16 66/171 |
| 2013/0019500 A1 | * | 1/2013 | Greene .............. A43B 23/025 36/50.1 |
| 2013/0219749 A1 | * | 8/2013 | Dojan ............... A43B 23/0275 36/83 |
| 2014/0283410 A1 | * | 9/2014 | Marvin .............. A43B 23/0255 36/45 |
| 2014/0310983 A1 | | 10/2014 | Tamm et al. |
| 2015/0216256 A1 | * | 8/2015 | Podhajny ............. A43C 1/00 36/84 |
| 2015/0272274 A1 | * | 10/2015 | Berns ............... A43B 23/0205 36/84 |
| 2015/0359290 A1 | * | 12/2015 | Podhajny ........... D04B 1/123 36/9 R |
| 2017/0340064 A1 | * | 11/2017 | Boucher ........... A43B 23/0215 |
| 2017/0370027 A1 | | 12/2017 | Da Costa Pereira Machado et al. |
| 2017/0370034 A1 | * | 12/2017 | Kuo .................... D04B 15/90 |

FOREIGN PATENT DOCUMENTS

| | | |
|---|---|---|
| CN | 104919101 A | 9/2015 |
| CN | 105239261 A | 1/2016 |
| CN | 105533889 A | 5/2016 |
| CN | 105747351 A | 7/2016 |
| CN | 105996284 A | 10/2016 |
| DE | 10 2015 116 398 A1 | 3/2017 |
| EP | 3 070 192 A1 | 9/2016 |
| TW | 201531250 A | 8/2015 |
| TW | M579471 U | 6/2019 |
| WO | WO 2015/116295 A1 | 8/2015 |

OTHER PUBLICATIONS

Office Action dated Feb. 10, 2020 for Taiwan Application No. 107127173, 23 pages.
International Preliminary Report on Patentability in Application No. PCT/US2018/045163, dated Feb. 4, 2020, 9 pages.
Office Action and English Translation in Corresponding Chinese Application No. 2020201393865, dated Sep. 24, 2020 (4 pages).
Office Action received for European Patent Application No. 18756123.8, dated Feb. 23, 2021, 5 pages.
Intention to Grant received for European Patent Application No. 18756123.8, dated Sep. 8, 2021, 8 pages.

* cited by examiner

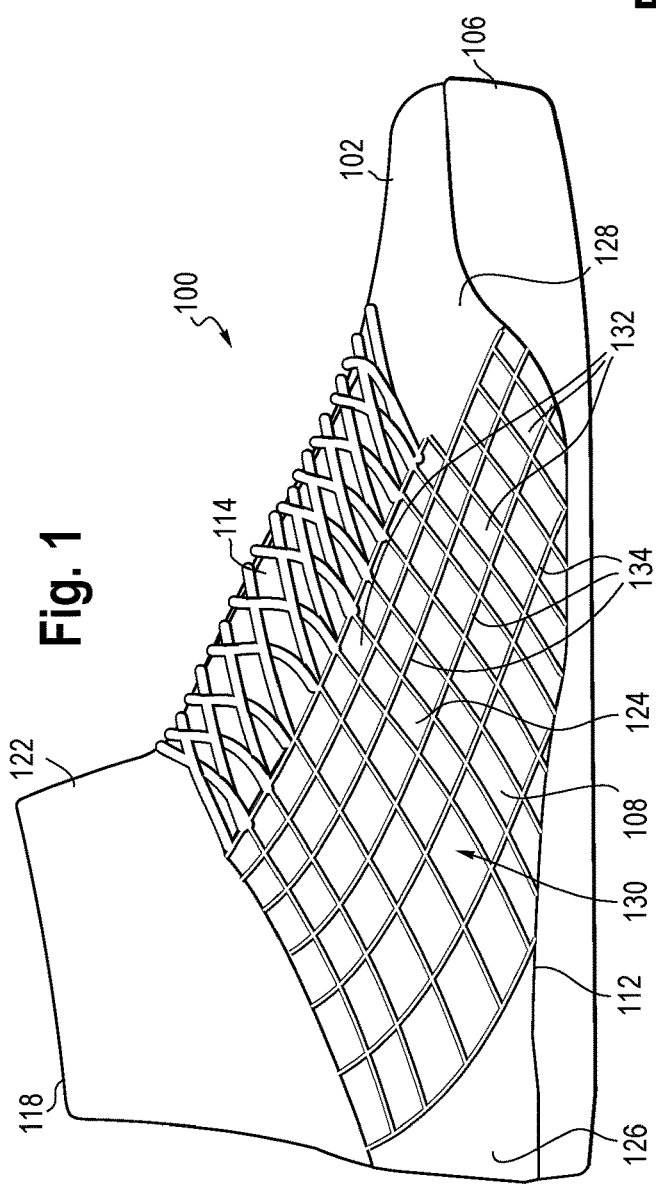
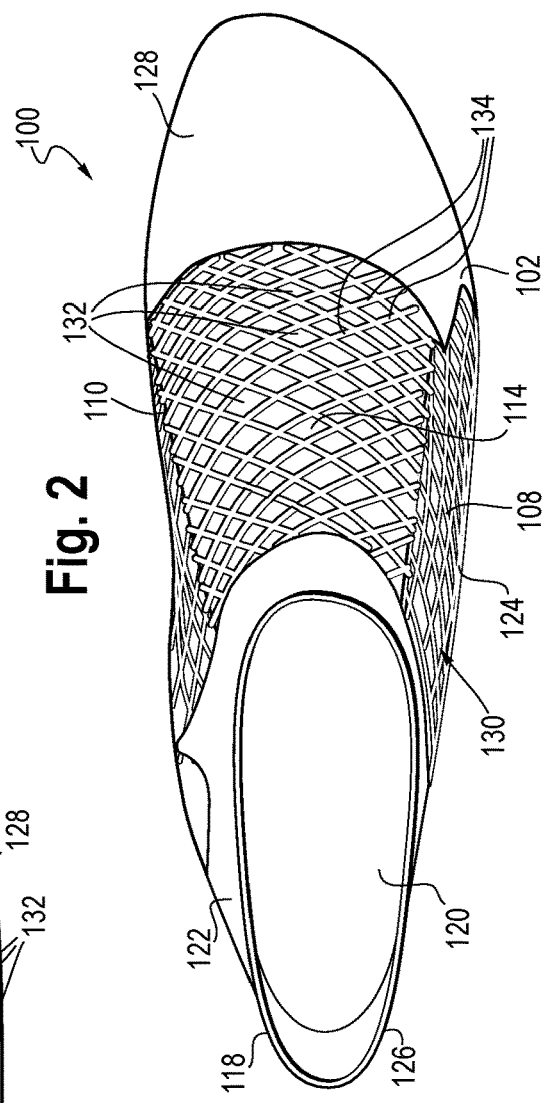

ARTICLE WITH AT LEAST ONE LAYERED POD

RELATED APPLICATIONS

This application claims the benefit of U.S. Provisional Application No. 62/541,500, filed Aug. 4, 2017, which is hereby incorporated by reference in its entirety.

FIELD

The disclosure is directed to articles, including articles of footwear and articles of apparel, having at least one layered pod. The layered pod may be formed by a knitted component or other textile. More specifically, the disclosure relates to articles of footwear and components thereof having a layered pod.

BACKGROUND

Conventional articles of footwear generally include two primary elements: an upper and a sole structure. The upper is generally secured to the sole structure and may form a void within the article of footwear for comfortably and securely receiving a foot. The sole structure is generally secured to a lower surface of the upper so as to be positioned between the upper and the ground. In some articles of athletic footwear, for example, the sole structure may include a midsole and an outsole. The midsole may be formed from a polymer foam material that attenuates ground reaction forces to lessen stresses upon the foot and leg during walking, running, and other ambulatory activities. The outsole may be secured to a lower surface of the midsole and may form a ground-engaging portion of the sole structure that is formed from a durable and wear-resistant material.

The upper of the article of footwear generally extends over the instep and toe areas of the foot, along the medial and lateral sides of the foot, and around the heel area of the foot and in some instances under the foot. Access to the void in the interior of the upper is generally provided by an ankle opening in and/or adjacent to a heel region of the footwear. A lacing system is often incorporated into the upper to adjust the fit of the upper, thereby facilitating entry and removal of the foot from the void within the upper. In addition, the upper may include a tongue that extends under the lacing system to enhance adjustability of the footwear, and the upper may incorporate other structures such as, for example, a heel counter to provide support and limit movement of the heel.

BRIEF SUMMARY

In one aspect, the present disclosure provides knitted component comprising with a first surface and a second surface, the first surface facing opposite the second surface. A pod may have the first surface and the second surface, and an edge region may have the first surface and the second surface, where the edge region at least partially demarcates the pod. A first yarn may substantially form the first surface of the pod, where the first yarn is a fusible yarn. A second yarn may substantially form the second surface of the pod, and the second yarn may substantially form the first surface of the edge region.

In another aspect, the present disclosure provides an article formed of a knitted component. The article may include a first surface and a second surface, the first surface facing opposite the second surface. A pod may include the first surface and the second surface, and an edge region may have the first surface and the second surface, where the edge region at least partially demarcates the pod. A first material may substantially form the first surface of the pod, where the first material is a fusible material included in a first yarn. A second yarn may substantially form the second surface of the pod, and the second yarn may substantially form first surface of the edge region.

In another aspect, the present disclosure provides an article formed of a knitted component. The article may include a first surface and a second surface, the first surface facing opposite the second surface. A pod may have the first surface and the second surface, and an edge region may have the first surface and the second surface. The edge region may at least partially demarcate the pod. A first material may substantially form the first surface of the pod, where the first material is a fusible material included in a first yarn. A second yarn may substantially form the second surface of the pod, where a second material is inlayed between the first surface and the second surface of the pod.

BRIEF DESCRIPTION OF THE DRAWINGS

FIG. 1 is an illustration showing a lateral side view of an example of an article of footwear having pods in accordance with certain aspects of this disclosure.

FIG. 2 is an illustration showing a top view of the article of footwear depicted in FIG. 1.

DETAILED DESCRIPTION

Figure 3:
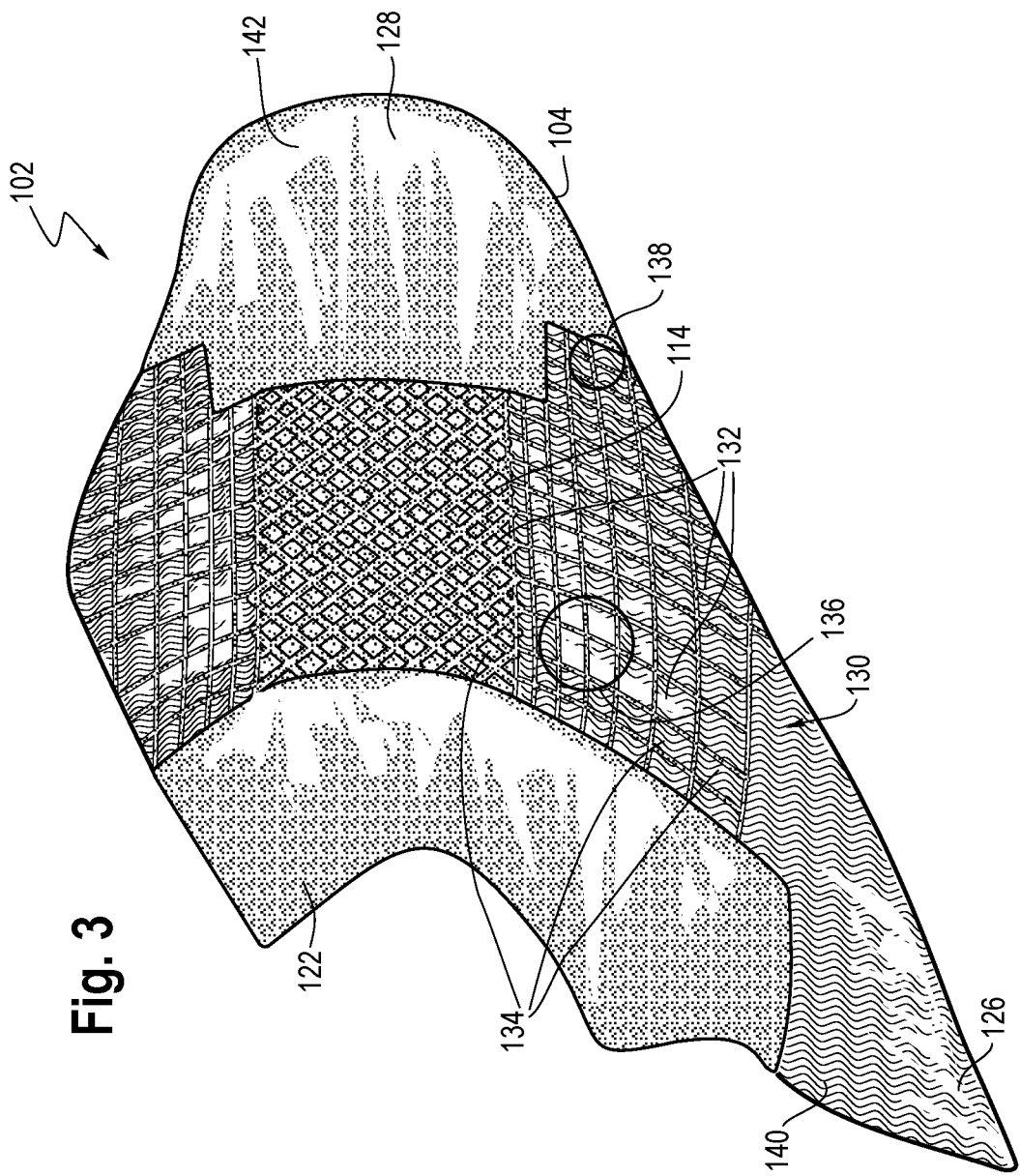
FIG. 3 is an illustration showing a top view of a knitted component for forming an upper of the article of footwear of FIGS. 1-2.

Various aspects are described below with reference to the drawings in which like elements generally are identified by like numerals. The relationship and functioning of the various elements of the aspects may better be understood by reference to the following detailed description. However, aspects are not limited to those illustrated in the drawings or explicitly described below. It also should be understood that the drawings are not necessarily to scale, and in certain instances details may have been omitted that are not necessary for an understanding of aspects disclosed herein, such as conventional fabrication and assembly.

Certain aspects of the present disclosure relate to uppers configured for use in an article of footwear and/or other articles, such as articles of apparel. When referring to articles of footwear, the disclosure may describe basketball shoes, running shoes, biking shoes, cross-training shoes, football shoes, golf shoes, hiking shoes and boots, ski and snowboarding boots, soccer shoes, tennis shoes, and/or walking shoes, as well as footwear styles generally considered non-athletic, including but not limited to dress shoes, loafers, and sandals.

FIG. 1 is an illustration showing an article of footwear 100, and FIG. 2 is a top view of the article of footwear 100. Referring to FIGS. 1-2, the article of footwear 100 may include an upper 102, where the upper 102 is substantially formed as a textile component. The textile component may be any suitable type of textile, and in some embodiments it may be formed as a knitted component. As shown, the upper 102 may be secured to a sole structure 106. The upper 102 may include a lateral side 108 and a medial side 110. The area where the sole structure 106 joins the upper 102 may be referred to as a biteline 112. The upper 102 may be joined to the sole structure 106 in a fixed manner using any suitable technique, such as through the use of an adhesive, by sewing, etc. The upper 102 may extend partially or completely around a foot of a wearer and/or may be integral with the sole structure 106, and a sockliner may or may not be used. In some embodiments, the sole structure 106 may include a midsole (not shown) and an outsole. The upper 102 may extend under the foot of a wearer and form an underfoot portion, which may be in place of the sole structure 106, if desired.

The upper 102 may additionally include a throat area 114 extending from and an ankle opening 118 leading to the void 120, and a collar 122 may at least partially surround an ankle opening 118. The void 120 of the article of footwear 100 may be configured (e.g., sized and shaped) to receive and accommodate a foot of a person. The throat area 114 may be generally disposed in a midfoot area 124 of the upper 102. The midfoot area 124 of the upper 102 may be located between a heel area 126 and a toe area 128. In some embodiments, an optional tongue (such as the tongue 276 shown in FIG. 8) may be disposed at least partially in the throat area 114, but no tongue is depicted in FIGS. 1-2. If a tongue is included, the tongue may be any type of tongue, such as a gusseted tongue or a burrito tongue. If a tongue is not included, the lateral and medial sides of the throat area 114 may be joined together.

As depicted in FIGS. 1-2, an outer surface 130 of the upper 102 be subdivided into two or more generally defined areas referred to as pods 132. The pods 132 may be at least partially demarcated by edge regions 134 of the upper 102. In some embodiments, the edge regions 134 may substantially or completely surround at least some of the pods 132. Within a given pod 132, the outer surface 130 may be formed primarily of a fused area of material that is heat-processed during the manufacturing of the article of footwear 100. Herein a "fused area" is an area where distinct portion(s) of material forming the upper (e.g., distinct individual strands or yarns formed of thermoplastic polymer material) are partially or substantially melted and then cooled such that the material is bonded together. A fused area is not required to be formed by any specific process. More specific constructions of the pods 132 and the surrounding edge regions 134 are described in further detail below.

At least a portion of the upper 102 may be formed by a knitted component 104 (and at least a portion of the knitted component may be referred to as a "knit element"). FIG. 3 shows the knitted component 104 as it may appear after knitting (e.g., on a flat knitting machine) but before being lasted or otherwise manipulated into a wearable shape in the depicted article of footwear 100 of FIGS. 1-2. While the upper 102 is described herein as being formed primarily of the knitted component 104, it alternatively or additionally could include a textile component formed by a process other than knitting (e.g., weaving) and may also include other materials including but not limited to leather, plastics, rubbers, and any other materials suitable for incorporation into the upper of an article of footwear.

Forming the upper 102 with the knitted component 104 may provide the upper 102 with advantageous characteristics including, but not limited to, a particular degree of elasticity (for example, as expressed in terms of Young's modulus), breathability, bendability, strength, moisture absorption, weight, abrasion resistance, and/or a combination thereof. These characteristics may be accomplished by selecting a particular single layer or multi-layer knit structure (e.g., a ribbed knit structure, a single jersey knit structure, or a double jersey knit structure), by varying the size and tension of the knit structure, by using one or more yarns formed of a particular material (e.g., a polyester material, a relatively inelastic material, or a relatively elastic material such as spandex), by selecting yarns of a particular size (e.g., denier), and/or a combination thereof.

The knitted component 104 may also provide desirable aesthetic characteristics by incorporating yarns having different colors, textures or other visual properties arranged in a particular pattern. The yarns themselves and/or the knit structure formed by one or more of the yarns of the knitted component 104 may be varied at different locations such that the knitted component 104 has two or more portions with different properties (e.g., a portion forming the throat area 114 of the upper 102 may be relatively elastic while another portion may be relatively inelastic). In some embodiments, the knitted component 104 may incorporate one or more materials with properties that change in response to a stimulus (e.g., temperature, moisture, electrical current, magnetic field, or light). For example, the knitted component 104 may include yarns formed of one or more thermoplastic polymer materials (including material composites) that transition from a solid state to a softened or liquid state when subjected to certain temperatures at or above its melting point and then transitions back to the solid state when cooled. The thermoplastic polymer material(s) may provide the ability to heat and then cool a portion of the knitted component 104 to thereby form an area of bonded or continuous material (herein referred to as a "fused area") that exhibits certain advantageous properties including a relatively high degree of rigidity, strength, and water resistance, for example. Non-limiting examples of thermoplastic polymer materials are polyurethanes, polyamides, polyolefins, and/or nylons.

As shown in FIG. 3, the knitted component 104 may substantially form the pods 132 and the surrounding edge regions 134. When thermoplastic polymer material is included and configured to be fused during a heat-processing step, the thermoplastic polymer material may be exposed on the outer surface 130 of the knitted component 104 only at the pods 132, and other materials may be used to form the outer surface 130 at the edge regions 134. Thus, once heat is applied to the outer surface 130 during a heat-processing step (e.g., steaming or otherwise applying heat after knitting), the result of this process may be the formation of a "shell" on the outer surface 130 of the pods 132. The shell may enhance the stiffness, strength, rigidity, durability, and other characteristics of the article of footwear 100. The enhanced characteristics may provide additional support and structure and may bolster or replace other structural elements (such as a heel counter, brio cables, etc.). Certain methods of heat-processing an outer surface of a knitted component are described in detail in U.S. patent application Ser. No. 15/443,808, filed Feb. 27, 2017, which is herein incorporated by reference in its entirety.

In some embodiments, the heat-processing of the outer surface 130 of the pods 132 may cause the melted thermoplastic polymer material to flow over the edge regions 134 such that the edge regions 134 are at least partially covered by fused material once it has cooled. Alternatively, the fused material may be isolated on the outer surface 130 only adjacent to the pods 132 and may terminate adjacent to the edge regions 134 leaving at least a portion of the outer surface 130 free of the fused material at the edge regions 134. Thus, at least after heat-processing, the edge regions 134 may have a first degree of flexibility, the pods 132 may have a second degree of flexibility, and the first degree of flexibility may be substantially greater than the second degree of flexibility (which may be at least partially attributed to the lack of fused material on the edge regions 134). Similarly, the edge regions 134 may have a first degree of stiffness, the pods 132 may have a second degree of stiffness, and the first degree of stiffness may be substantially less than the second degree of stiffness. The relative degrees of flexibility and stiffness may be compared by applying a force to the respective components and then measuring the amount of displacement through those same components.

Different pods 132 may have identical dimensions, but at least some of the pods 132 may have dimensions that are substantially different. Similarly, the edge regions 134 may be about the same size throughout the knitted component 104, but alternatively the edge regions 134 may vary in size. The sizes and locations of the pods 132 and/or the edge regions 134 may thus be selected to provide the upper 102 with strength, rigidity, protection, and other characteristics where desired, while also providing suitable flexibility, stretchability, and other characteristics at other zones or locations. To illustrate, the pods 132 in a first zone 136 may be larger, on average, than the pods 132 located in a second zone 138, where the first zone 136 is located closer to the heel area 126 and the second zone 138 is located closer to the toe area 128. Thus, the edge regions 134 may be more prevalent in the second zone 138 than the first zone 136 per unit area. As a result, the first zone 136 may have a higher degree of strength, rigidity, durability, and stiffness (along with other characteristics associated with the pods 132) while the second zone 138 may have a higher degree of flexibility, stretchability, and other characteristics associated with the edge regions 134. It is also contemplated that different pods 132 may have different material compositions such that, even correcting for size, the pods 132 provide differing degrees of the associated characteristics. To illustrate, a first pod may have a greater density of a thermoplastic polymer material on the outer surface 130 than a different second pod, and as a result, the first pod may have a greater degree of stiffness than the second pod.

While not required in all embodiments, it is contemplated that the substantial entirety of the heel area 126 may be constructed in a manner similar to the construction of the pods 132 (e.g., such that one large pod 140 forms the majority of the heel area 126). Similarly, substantially the entirety of the toe area 128 may be formed by a large pod 142. Advantageously, the heel area 126 and/or the toe area 128 may bolster or replace heel counter and/or toecap elements to thus offer a degree of desirable rigidity, strength, and structural support to a wearer etc. that is desirable in certain applications. In contrast, other portions such as the collar 122 may be formed with an elastic knit structure, and/or may not be heat-processed, such that the collar 122 is configured to stretch when receiving a foot.

Figure 4:
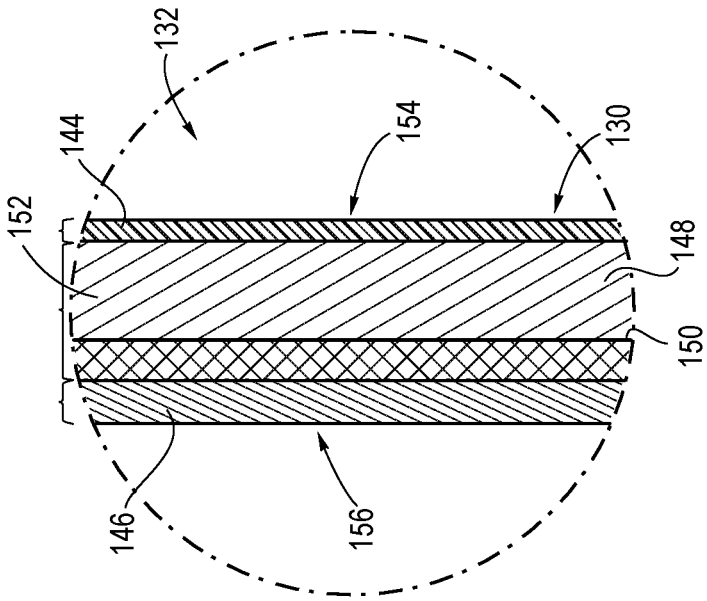
FIG. 4 is an illustration showing a side cutout view of a pod included in an upper in accordance with the present disclosure, where the pod has three layers.

Whether formed of the knitted component 104 or not, the upper 102 may have a single layer or multiple layers. For example, as shown in FIG. 4 (showing a side cutout view of one of the pods 132), at least one pod 132 of the upper 102 may include a first layer 144 and a second layer 146, where the first layer 144 is an outer layer and the second layer 146 is an inner layer nearer the void when incorporated into the article of footwear 100. The knitted component may also have the first surface 154 formed by the first layer 144 (which may include the outer surface 130 of FIGS. 1-3) and the second surface 156 formed by the second layer 146. The second surface 156 and the first surface 154 may face in opposite directions. For example, the first surface 154 may face outward (e.g., such that it is exposed for viewing when the article of footwear 100 is in use), and the second surface 156 may face the void, or interior of the article of footwear 100.

Figure 5:
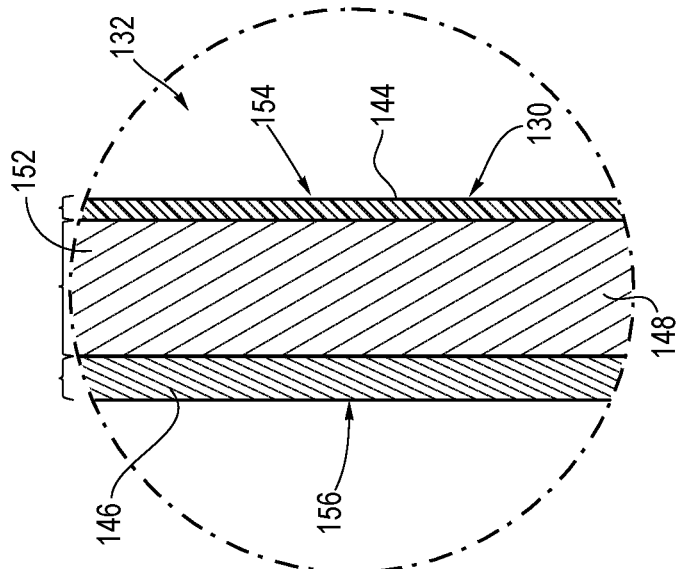
FIG. 5 is an illustration showing a side cutout view of a pod included in an upper in accordance with the present disclosure, where the pod has four layers.

The first layer 144 may include the above-described fused area, such that it can be considered to have formed a "shell" for providing protection and other desirable properties for the outer surface 130, and the second layer 146 may be formed of a material (e.g., elastane, cotton, or polyester) having desirable comfort-related characteristics for contacting a foot or sock of a wearer, such as a desirable elasticity, absorption and/or anti-abrasiveness. A third layer 148 may be located in a pocket 152 that is formed between the first layer 144 and the second layer 146. As described in more detail below, if the upper 102 is formed of a knitted component 104, the third layer 148 may include an inlaid material located at least partially between the first layer 144 and the second layer 146, where the first layer 144 and the second layer 146 are both knitted layers. The third layer 148 may be substantially bonded to the first layer 144 due to heat processing of the material of the first layer 144, but this is not required. More or fewer than three layers are also contemplated. For example, as shown in FIG. 5, a fourth layer 150 may be located between the second layer 146 and the third layer 148, but the fourth layer 150 may alternatively be located in any other location.

In some embodiments, the fused material forming the first layer 144 may be transparent (at least after heat-processing) such that when a viewer looks at the first surface 154, he or she can detect the visual characteristics of the underlying third layer 148. The third layer 148 can be formed/manipulated during the manufacturing process to provide desirable visual effects without limitation, as the third layer 148 may not have the necessity of providing structural characteristics (which may instead be substantially provided by the first layer 144). However, it is also contemplated that the third layer 148 may provide certain structural or other functional characteristics, if desired, such as cushioning. Similarly, the fourth layer 150 may provide cushioning and/or other characteristics, such as additional stiffness, or alternatively, such as a water resistant layer, for example, that may be desired in the upper 102. In some embodiments, the thermoplastic polymer material of the first layer 144 may not be transparent prior to the heat-processing step, and instead may have a color or may be opaque (e.g., white) and may hide or otherwise obscure the third layer 148 from view. This may be advantageous where it is beneficial to easily view the position of the material forming the first layer 144 during manufacturing to ensure quality standards are met.

Figure 6:
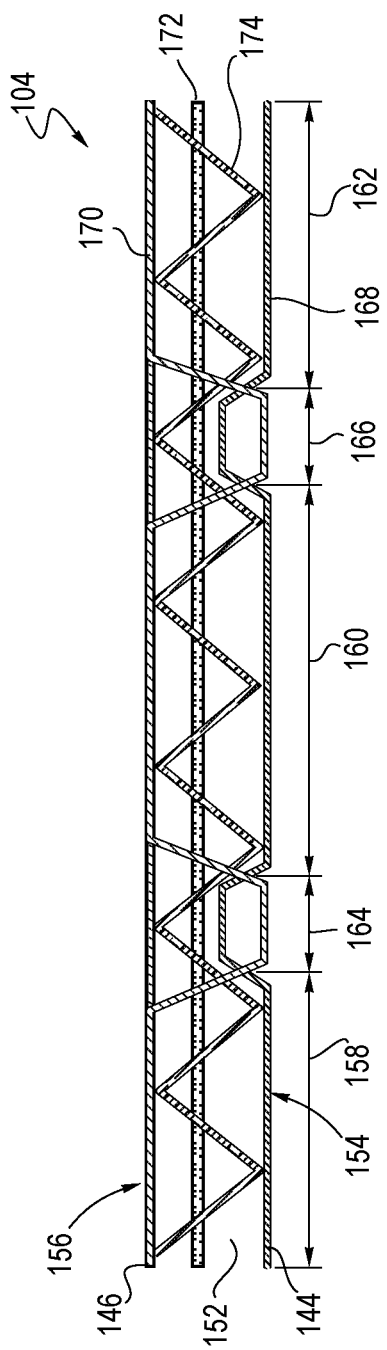
FIG. 6 is an illustration showing a side cutout view of three pods separated by two edge regions of a knitted component in accordance with the present disclosure.

FIG. 6 is an illustration showing a detailed side-cutout view of a multi-layer knitted component 104 forming the upper 102. The depicted knitted component 104 has a first pod 158, a second pod 160, and a third pod 162. The first pod 158 and the second pod 160 may be separated by a first edge region 164, and the second pod 160 and the third pod 162 may be separated by a second edge region 166. For illustration purposes, in FIG. 6, four yarns (e.g., yarn types having one or more strands) are included: a first yarn 168, a second yarn 170, a third yarn 172, and a fourth yarn 174.

While the yarns 168, 170, 172, 174 can be made of any suitable material, in an exemplary embodiment, the first yarn 168 may be at least partially formed with a thermoplastic polymer material having a suitable melting point that is substantially lower than the melting point and decomposition point of the second yarn 170 (for example, 100° C. lower or more) and also substantially lower than the melting point and decomposition point of the third yarn 172 and fourth yarn 174. Illustrative, non-limiting examples of suitable thermoplastic polymer materials include polyurethanes, polyamides, polyolefins, and nylons. In some embodiments, substantially the entirety of the first yarn 168 may be formed of the thermoplastic polymer material, but alternatively the first yarn 168 may be a yarn with a thermoplastic polymer sheath with a relatively low melting point surrounded by a core that remains stable at higher temperatures. The melting temperature of the thermoplastic polymer material may be, for example, between about 80° C. and about 200° C., such as from about 100° C. to about 125° C. based on atmospheric pressure at sea level. In another embodiment, the thermoplastic polymer may be a nylon co-polymer with a melting point of between about 130° C. and about 150° C., such as about 140° C. Additionally or alternatively, the first yarn 168 may include a thermoplastic polyurethane. Additionally or alternatively, the thermoplastic polymer material may be formed of a material that becomes translucent or transparent when raised above its melting point and then cooled.

The second yarn 170 may be made from a yarn substantially formed of polyester or a polyester in combination with elastane. Such a yarn may provide elasticity and anti-abrasion that is well suited for forming the inner surface of an upper. The melting point or decomposition point of the material(s) forming the second yarn 170 may be relatively high (e.g., above 200° C. or higher, such as 260° C. or higher for certain polyesters) such that the material remains stable during heat processing of the knitted component 104.

Like the second yarn 170, the depicted third yarn 172 may be formed of a material that remains stable during heat processing. In one embodiment, the third yarn 172 may comprise a plurality of polyester yarns having different colors. Advantageously, the third yarn 172 may provide a desirable visual effect when the first yarn 168 forms a transparent shell on the first surface 154 (as described in more detail below). Optionally, the third yarn 172 may additionally or alternatively be formed of a material that provides loft within the pockets 152 to provide the knitted component 104 with a visually-appealing texture where the pods 132 extend outward with respect to the edge regions 134. In one non-limiting embodiment, the third yarn 172 may include a bulking material that expands in size after the knitting process (e.g., in response to a stimulus, such as heat), thus enhancing the optional loft provided within the pod 132. Such yarns are described in detail in U.S. Provisional Application No. 62/355,153, filed Jun. 27, 2016, and U.S. Provisional application Ser. No. 15/631,344, filed Jun. 23, 2017, each of which is incorporated by reference herein in its entirety.

The fourth yarn 174 may be a monofilament yarn, which may be advantageous for providing a durable and inelastic tie (as described in more detail below). Monofilament yarns are formed of a single elongated, continuous filament of a synthetic polymer material. Some monofilament yarns, such as those made of a single filament of an inelastic synthetic polymer material may have substantially no elasticity, or very little, elasticity. For example, a monofilament yarn made of an inelastic synthetic polymer material may have maximum elongation of less than 5% (e.g., the maximum length of the yarn when subjected to a tensile force approaching its breaking force is less than 105% of its length when not subjected to a tensile force), and it is contemplated that a such a yarn could have a maximum elongation of 1%, 0.5%, or even less.

Referring to the knit construction illustrated in FIG. 6, the knitted component 104, including each of the depicted pods and edge regions, may include the first surface 154 (e.g., an outward-facing surface) and the second surface 156. Referring to the second pod 160, the first surface 154 may be formed substantially by the first yarn 168 such that, when heat-proces172 issed, the fusible material of the first yarn 168 fuses to form a rigid first surface 154. In contrast, the first surface 154 of the first edge region 164 may be substantially formed by the second yarn 170. If the second yarn 170 is substantially free of fusible material, and/or the material of the second yarn 170 has a melting point that is higher than a melting point of the first yarn 168, the edge regions 164, 166 may remain relatively flexible with respect to the first pod 158 after heat processing (at least on the first surface 154). Similarly, the first surface 154 of the second edge region 166 may be substantially formed of the second yarn 170 and also remain relatively flexible with respect to the second pod 160 and third pod 162 after heat processing (at least on the first surface 154).

The second surface 156 of the knitted component may be substantially formed of the second yarn 170 throughout the depicted pods and edge regions. Advantageously, when the second yarn 170 is a polyester yarn, for example, the second layer 146 may have characteristics that are desirable for facing a void. For example, the second surface 156 may have relative softness and/or other comfort-related characteristics that are suitable and desirable for contacting the foot or sock of a wearer. As described in more detail below, this construction may be achieved by utilizing a knitting process that forms a multi-layer structure. For example, within the first, second, and/or third pods 158, 160, 162, the first layer 144 having the first surface 154 may be substantially formed on a first needle bed of a flat knitting machine, and the second layer 146 having the second surface 156 may be substantially formed on a second bed of the flat knitting machine such that the pocket 152 is formed between the first layer 144 and the second layer 146. At least a portion of the second yarn 170 may be knit with the first needle bed at the edge regions 164, 166. Other suitable knitting processes are also contemplated (e.g., a technique utilizing transfers between both needle beds). A specific knitting process is described in more detail below with reference to FIG. 7.

The third yarn 172 may be a yarn that is inlaid between the first layer 144 and the second layer 146. While only one third yarn 172 is depicted in FIG. 6, a plurality of yarns may be inlaid between the first layer 144 and the second layer 146, and thus the depicted third yarn 172 may represent a plurality of yarns in reality (e.g., a plurality of yarn types, and/or a plurality of individual yarns of the same type). The third yarn 172 may have one or more visual characteristics to provide the knitted component 104 with desirable visual properties. For example, when the knitted component 104 is viewed from a perspective looking towards the first surface 154, the third yarn 172 may be visible within at least one of the pods 158, 160, 162 due to the transparency of the material of the heat-treated first yarn 168. Thus, it is contemplated that the third yarn 172 may include a variety of colors, visual textures, patters, or other visual properties that may be deemed visually appealing. Optionally, a material (e.g., a material other than a yarn) may be included within the pocket 152 as an alternative to, or in addition to, the third yarn 172. Such a material may enhance the padding or cushioning-related characteristics of the pod. Alternatively, such material may enhance the rigidity or stiffening characteristics of the pod to provide greater structure to the particular region. Once the first yarn 168 is heat-processed, the thermoplastic polymer material of the first yarn 168 may be at least partially bonded to the third yarn 172.

Optionally, the fourth yarn 174 may be included to provide a tie (e.g., a structural connection) between the first layer 144 and the second layer 146 within the pods 158, 160, 162. The fourth yarn 174 may thus be advantageous for providing the pods 158, 160, 162 with structural integrity and/or for reducing movement of the third yarn 172 within the pod. In some embodiments, and as described above, the fourth yarn 174 may be a monofilament yarn or strand. Advantageously, since monofilament strands are often relatively small in diameter and formed of a transparent material while still having relatively high tenacity and strength, the fourth yarn 174 may provide an adequate tie between the layers 144, 146 without interrupting the visual characteristics provided by the inlaid third yarn 172. The resulting knit structure of the knitted component 104 may have suitable strength, durability, rigidity, and other desirable structural characteristics. In other embodiments, the fourth yarn 174 may be excluded such that the first layer 144 and the second layer 146 are separable at the pods 158, 160, 162.

Figure 7:
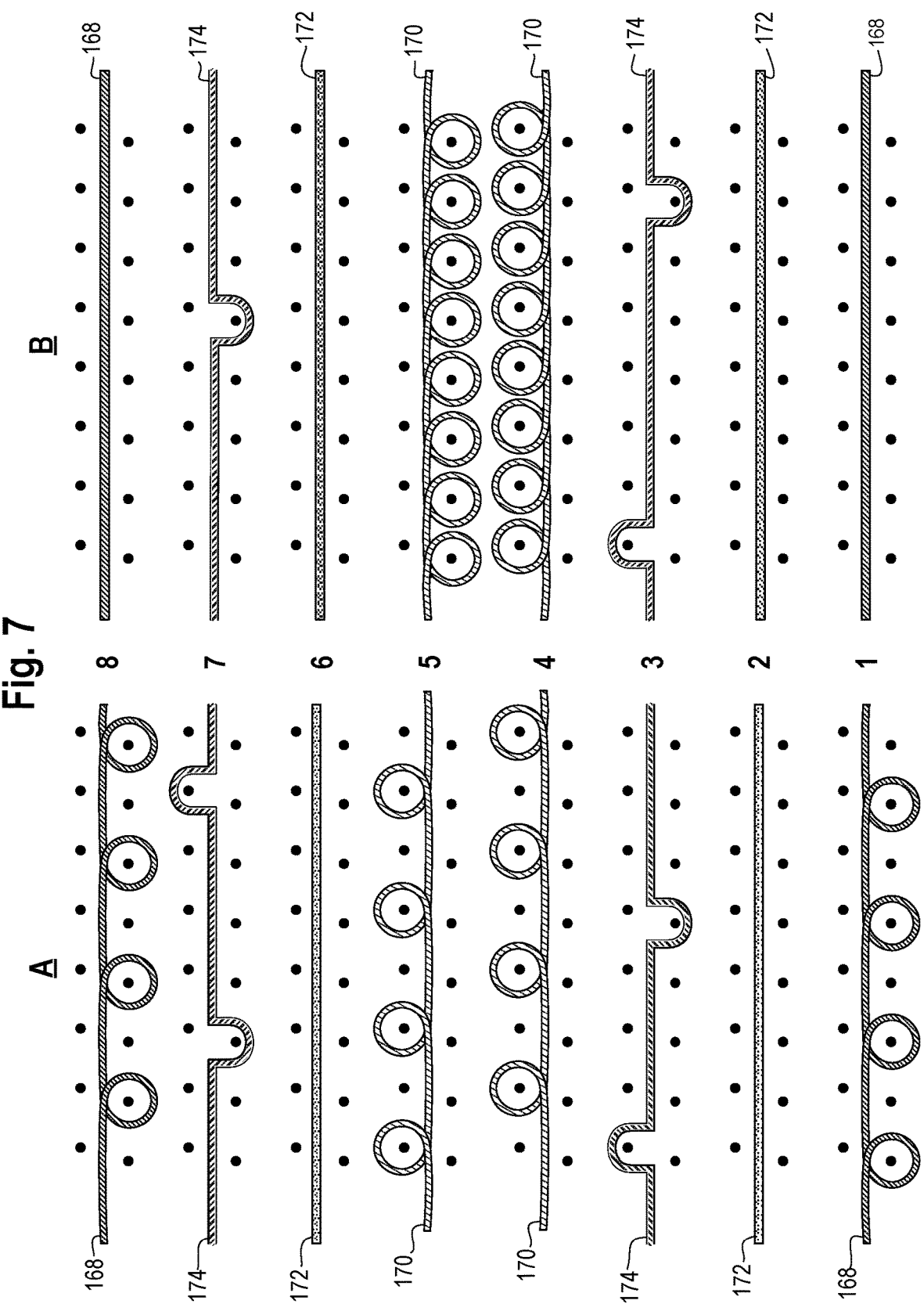
FIG. 7 is an illustration showing an example of a knitting process for forming a pod ("A") and an edge region ("B") of the knitted component of FIG. 6 on a knitting machine.

FIG. 7 illustrates exemplary knit diagrams for the pod and edge regions, respectively, and one skilled in the art would know how to accomplish it based on the diagrams alone. In one example, the sequence identified as "A" on the left side of FIG. 7 illustrates one embodiment of a knitting sequence that may be used for the pods 158, 160, 162 of the knitted component 104 as shown in FIG. 6. Similarly, the sequence identified as "B" on the right side of FIG. 7 illustrates a knitting sequence that may be used to form the edge regions 164, 166 of the knitted component 104. As is apparent to a person of ordinary skill in the art, the types of yarns and manner of knitting each yarn may differ between different areas of the knitted component 104, and the sequences depicted and described herein can be slightly or substantially altered to form similar structures.

Referring to sequence "A" of FIG. 7, step 1 represents one or more knitting passes of knitting the first yarn 168 on every other needle of a first needle bed (e.g., a front bed). In step 2, the third yarn 172 may be inlaid between the first needle bed and a second needle bed of the knitting machine. As described in more detail above, the third yarn 172 may represent a plurality of strands or yarns which may be inlaid with one pass or multiple passes. For example, in an exemplary embodiment, the third yarn 172 may include eight (8) inlaid polyester yarns having selected colors or other visual characteristics. In step 3, the fourth yarn 174 may be knit to anchor or secure (e.g., "tie") the first layer 144 to the second layer 146 using tuck stitching. In step 4, the second yarn 170 may be knitted on every other needle of the back bed, as shown, with the second yarn 170 again being knitted in step 5 on the alternate needles of the back bed. In step 6, the third yarn 172 may again be inlaid. In step 7, the fourth yarn 174 may again be knit to tie the first layer 144 to the second layer 146, using tuck stitches. Finally, in step 8, the first yarn 168 is knit on every other needle of the front bed that was not used in step 1. The resulting structure may be similar to at least one of the pods 158, 160, 162 depicted in FIG. 6.

Referring sequence "B" of FIG. 7, which may represent the formation of one of the edge regions 164, 166 (shown in FIG. 6), step 1 may include inlaying the first yarn 168. In step 2, the third yarn 172 may be inlaid. In step 3, the fourth yarn 174 may be knit to anchor the adjacent yarns using tuck stitching. In step 4, the second yarn 170 may be knitted on the back bed, as shown, with the elastic yarn again knitted in step 5 on the front bed. In step 6, the third yarn 172 may again be inlaid. In step 7, the fourth yarn 174 may again be knit to tie yarns using tuck stitches. Finally, in step 8 the first yarn 168 may be inlaid as shown.

Figure 8:
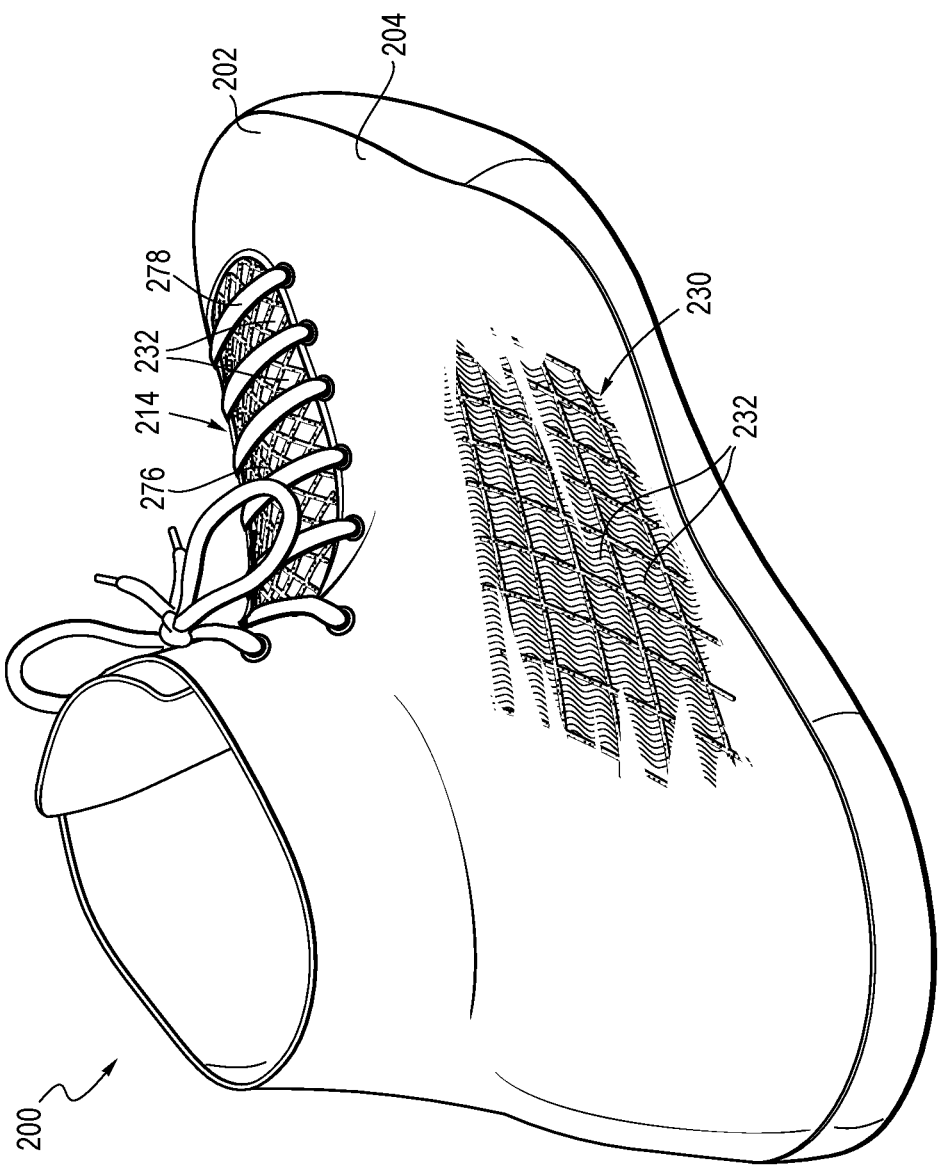
FIG. 8 is an illustration showing a top perspective view of another embodiment of an article of footwear having pods in accordance with certain aspects of the present disclosure.

FIG. 8 is an illustration showing a top perspective view of another embodiment of an article of footwear 200. As shown, the article of footwear 200 may include an upper 202 that is formed of a knitted component 204. The upper 202 may include a tongue 276 extending through a throat area 214 of the upper 202. The tongue 276 may be formed as a portion of the knitted component 204 on a knitting machine, or it may be separately formed and then later attached to the knitted component 204 after the knitting process (e.g., via sewing). The article of footwear 200 may also include a fastening element. Any suitable type of fastening element may be used, such as the depicted lace 278, a cable-tensioning system, and/or any other suitable device. The upper 202 may be configured to secure to and communicate with the fastening element such that the fastening element may adjust and/or tighten the upper 202 around a foot of a wearer. For example, the upper 202 may include a set of apertures for receiving the fastening element, but other suitable element(s) may alternatively be used.

Like certain embodiments described above, the knitted component 204 may include one or more pods 232. The pods 232 may incorporate any of the characteristics, constructions, or other features described with respect to the embodiments above. As shown, the pods 232 may be located on the knitted component 204 on an outer surface 230 of the upper 202 in a location other than in the throat area 214. Additionally or alternatively, the pods 232 may be located on the tongue 276. Advantageously, the pods 232 on the tongue 276 may provide protection, rigidity, cushioning, durability, and/or other related characteristics in the throat area 214 without sacrificing the ability of the upper 202 to be tightened around the foot.

Figure 9:
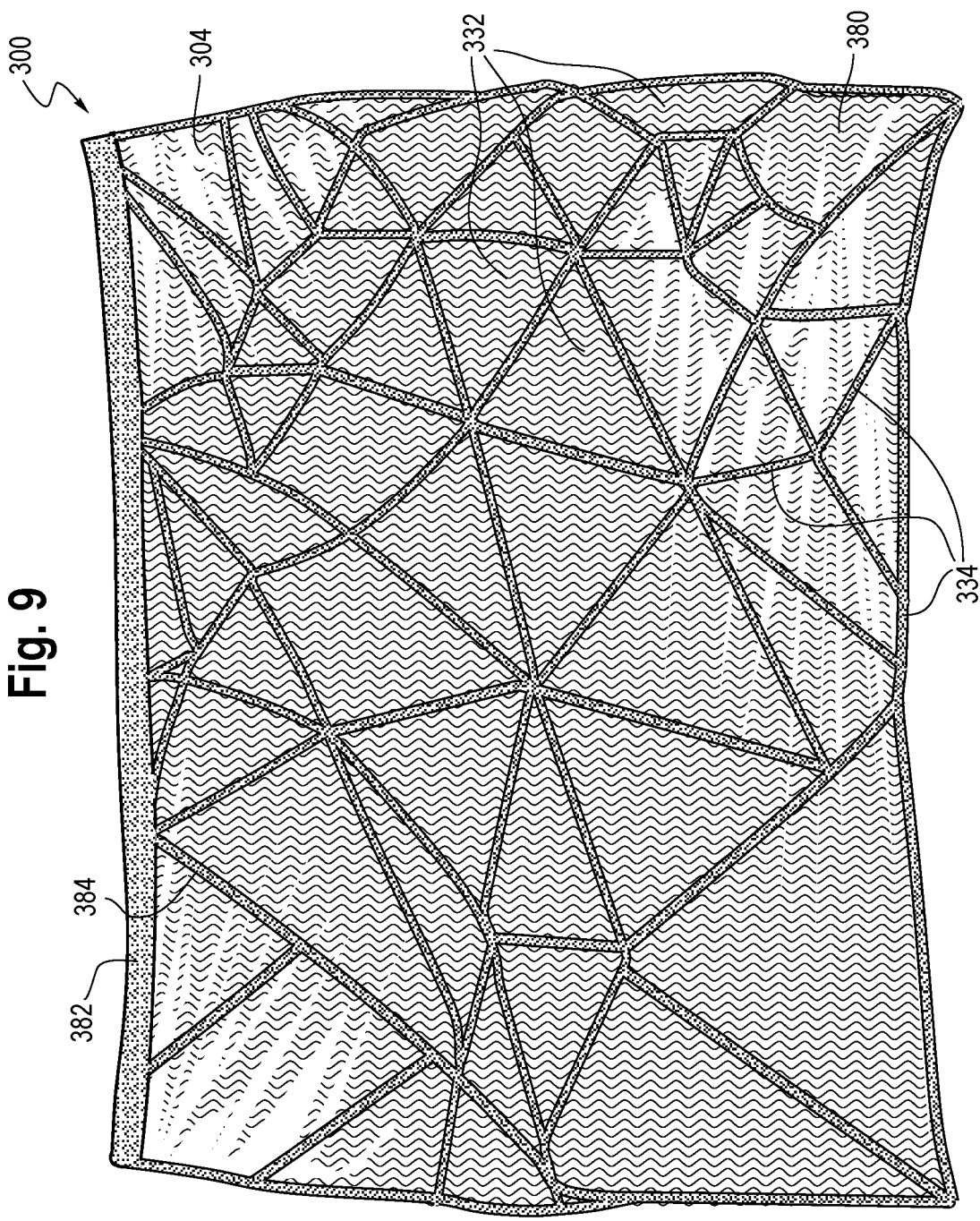
FIG. 9 is an illustration showing a top view of an embodiment of an article having pods in accordance with certain aspects of the present disclosure.

FIG. 9 is an illustration showing a top view of an embodiment of an article 300. The article 300 may be a swatch for an article of apparel. Non-limiting examples of articles of apparel include shirts, pants, socks, footwear, jackets and other outerwear, briefs and other undergarments, hats, and the like. Like the examples above, the article 300 may include a plurality of pods 332 surrounded by edge regions 334. In some embodiments, the article 300 may be substantially formed by a knitted component 304. The knitted component 304 may include a construction similar to the construction described with respect to the embodiments above, though other constructions are also contemplated. As shown, the pods 332 may include a variety of shapes and sizes. Certain pods 332 may be substantially formed as triangles, rectangles, pentagons, hexagons, etc. Optionally, at least some of the pods 332 may be demarcated by edge regions 334 that are curved, as shown (see, e.g., pod 380).

In some embodiments, dimensions of the edge regions 334 may vary. For example, a first edge region 382 may have a first thickness, a second edge region 384 may have a second thickness, and the first thickness may be greater than the second thickness. Advantageously, thicker edge regions may be placed in locations where more flexibility, stretchability, and/or other characteristics are desired. Similarly, larger pods 332 may be placed in locations where stiffness, rigidity and/or structure and other related characteristics are desired.

Figure 10:
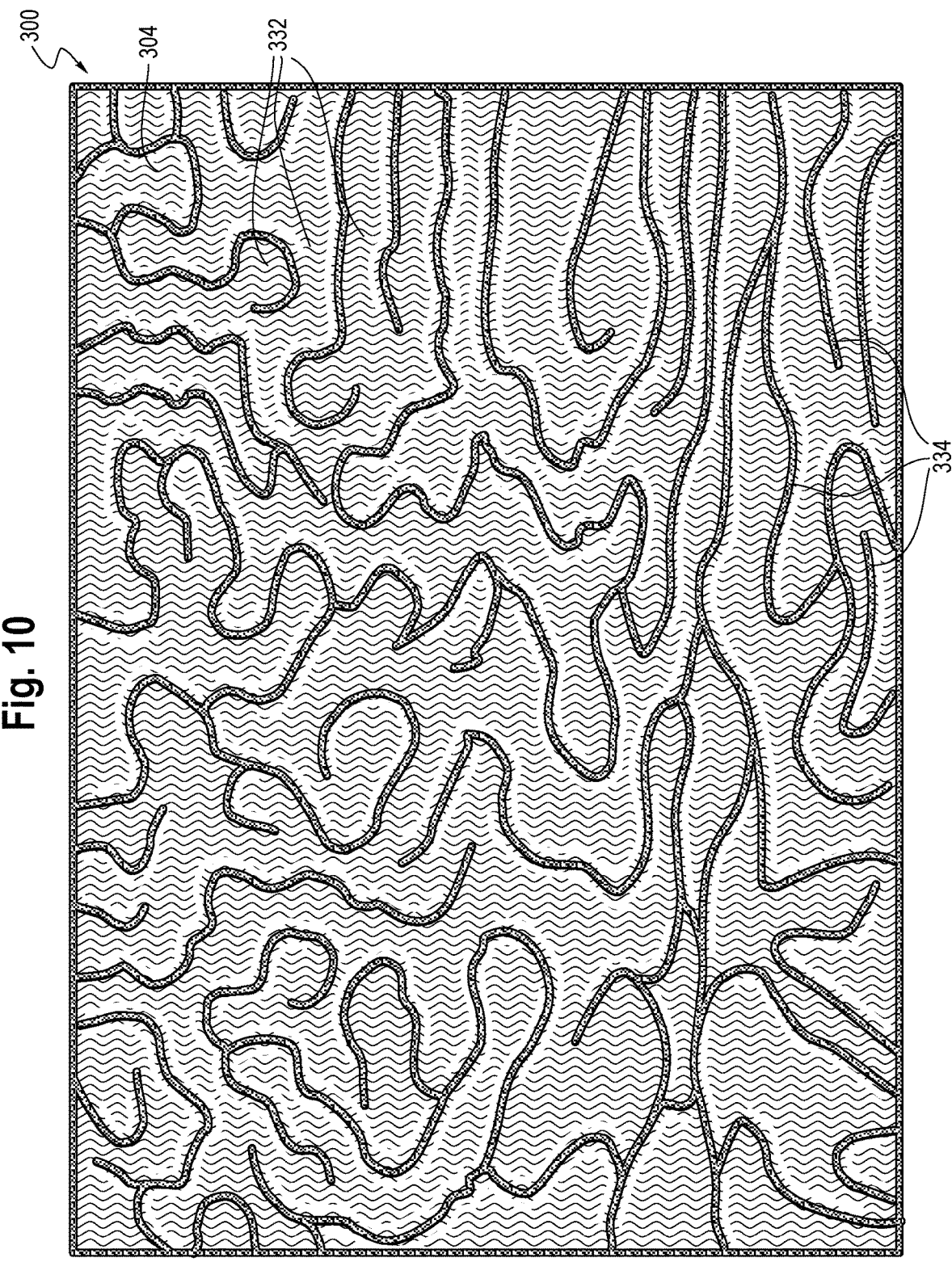
FIG. 10 is an illustration showing a top view of an embodiment of an article having irregular pods in accordance with certain aspects of the present disclosure.

Referring to FIG. 10, in some embodiments, the pods 332 of the article 300 may have an irregular shape (and in some embodiments, only one irregular pod may be included). For example, the edge regions 334 may extend in an irregular path (e.g., a curved, swerved, jagged, or otherwise non-linear path) through the knitted component 304 of the article 300.

All of the structures and methods disclosed and claimed herein can be made and executed without undue experimentation in light of the present disclosure. While this disclosure may be embodied in many different forms, there are described in detail herein specific aspects of the disclosure. The present disclosure is an exemplification of the principles of the disclosure and is not intended to limit the disclosure to the particular aspects illustrated. In addition, unless expressly stated to the contrary, use of the term "a" is intended to include "at least one" or "one or more." For example, "a yarn" is intended to include "at least one yarn" or "one or more yarns."

Any ranges given either in absolute terms or in approximate terms are intended to encompass both, and any definitions used herein are intended to be clarifying and not limiting. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the disclosure encompasses any and all possible combinations of some or all of the various aspects described herein. It should also be understood that various changes and modifications to the aspects described herein will be apparent to those skilled in the art. Such changes and modifications can be made without departing from the spirit and scope of the disclosure and without diminishing its intended advantages. It is therefore intended that such changes and modifications be covered by the appended claims.

We claim:

1. A knitted component, comprising:
   a first surface and a second surface, the first surface facing opposite from the second surface;
   a plurality of pods each comprising the first surface and the second surface;
   a plurality of edge regions each comprising the first surface and the second surface, each edge region at least partially demarcating at least one of the plurality of pods, wherein the plurality of pods and the plurality of edge regions define a pattern across the knitted component;
   a first yarn substantially forming the first surface of each of the plurality of pods, wherein the first yarn is fused, defining a fused area along the first surface of each of the plurality of pods; and
   a second yarn substantially forming the second surface of each of the plurality of pods, and the second yarn substantially forming the first surface of each of the plurality of edge regions and substantially forming the second surface of each of the plurality of edge regions,
   wherein the first yarn remains between the first surface and the second surface in each of the plurality of edge regions, and
   wherein each of the plurality of edge regions has a first degree of flexibility, and the fused area has a second degree of flexibility, the first degree of flexibility being greater than the second degree of flexibility.

2. The knitted component of claim 1, wherein each one of the plurality of pods includes a pocket located between the first surface and the second surface.

3. The knitted component of claim 1, wherein a material is inlayed between the first surface and the second surface of each of the plurality of pods, and wherein the material includes a plurality of inlaid yarns.

4. The knitted component of claim 1, further comprising a tie yarn extending between the first surface and the second surface within each of the plurality of pods, wherein the tie yarn is a monofilament strand.

5. The knitted component of claim 1, wherein the first yarn has a melting temperature that is lower than a melting temperature of the second yarn.

6. The knitted component of claim 1, further comprising a third yarn located between the first surface and the second surface of each of the plurality of pods, wherein the fused area is transparent or translucent, such that the third yarn is visible through the fused area.

7. An article formed of a knitted component, the article comprising:
   a first surface and a second surface, the first surface facing opposite from the second surface;
   a plurality of pods each comprising the first surface and the second surface;
   a plurality of edge regions each comprising the first surface and the second surface, each edge region at least partially demarcating at least one of the plurality of pods, wherein the plurality of pods and the plurality of edge regions define a pattern across the knitted component;
   a first material substantially forming the first surface of each of the plurality of pods, wherein the first material is a fusible material included in a first yarn, wherein the fusible material is fused; and
   a second yarn substantially forming the second surface of each of the plurality of pods, and the second yarn substantially forming the first surface of each of the plurality of edge regions and substantially forming the second surface of each of the plurality of edge regions such that the first yarn remains between the first surface and the second surface in each of the plurality of edge regions,
   wherein each of the plurality of edge regions has a first degree of flexibility, and the fusible material that is fused has a second degree of flexibility, the first degree of flexibility being greater than the second degree of flexibility.

8. The article of claim 7, wherein the fusible material that is fused is at least partially translucent or transparent.

9. The article of claim 7, wherein the first yarn comprises a thermoplastic polymer.

10. The article of claim 7, wherein each of the plurality of pods includes a pocket located between the first surface and the second surface.

11. The article of claim 7, wherein a third yarn is located between the first surface and the second surface of each of the plurality of pods, wherein the third yarn is visible through the fusible material that is fused.

12. The article of claim 11, wherein the third yarn has a different visual property than the first yarn.

13. The article of claim 12, wherein the different visual property is a different color.

14. The article of claim 7, further comprising a tie yarn extending between the first surface and the second surface within each of the plurality of pods.

15. The article of claim 14, wherein the tie yarn is a monofilament strand.

16. An article formed of a knitted component, the article comprising:
- a first surface and a second surface, the first surface facing opposite from the second surface;
- a plurality of pods each comprising the first surface and the second surface;
- a plurality of edge regions each comprising the first surface and the second surface, each edge region at least partially demarcating at least one of the plurality of pods, wherein the plurality of pods and the plurality of edge regions define a pattern across the knitted component;
- a first material substantially forming the first surface of each of the plurality of pods, wherein the first material is a fusible material included in a first yarn, wherein the fusible material is fused, and wherein the first yarn remains between the first surface and the second surface in each of the plurality of edge regions; and
- a second yarn substantially forming the second surface of each of the plurality of pods, the second yarn including a second material,
- wherein a third material is inlayed between the first surface and the second surface of each of the plurality of pods,
- wherein the first surface of each of the plurality of edge regions and the second surface of each of the plurality of edge regions are substantially formed by the second material, the second material having a melting point that is higher than a melting point of the fusible material that is fused, and
- wherein the second material has a first degree of flexibility, and the fusible material that is fused has a second degree of flexibility, the first degree of flexibility being greater than the second degree of flexibility.

17. The article of claim 16, wherein the third material includes a plurality of inlaid yarns.

18. The article of claim 16, wherein the fusible material that is fused is at least partially translucent or transparent.

19. The article of claim 18, wherein the third material comprises a third yarn having a different visual appearance than the fusible material that is fused.

* * * * *